United States Patent
Meggs et al.

(10) Patent No.: US 11,593,777 B2
(45) Date of Patent: Feb. 28, 2023

(54) COMPUTING SYSTEM FOR SHARING NETWORKS PROVIDING PAYMENT ALLOCATION BASED UPON ATTRIBUTE SCORING AND RELATED METHODS

(71) Applicant: SHARABLE, LLC, Melbourne, FL (US)

(72) Inventors: Anthony F. Meggs, Melbourne, FL (US); Pinaki Asher, West Melbourne, FL (US)

(73) Assignee: SHARABLE, LLC, Melbourne, FL (US)

( * ) Notice: Subject to any disclaimer, the term of this patent is extended or adjusted under 35 U.S.C. 154(b) by 337 days.

(21) Appl. No.: 16/881,528

(22) Filed: May 22, 2020

(65) Prior Publication Data
US 2020/0372479 A1    Nov. 26, 2020

Related U.S. Application Data

(60) Provisional application No. 62/851,282, filed on May 22, 2019, provisional application No. 62/851,279,
(Continued)

(51) Int. Cl.
*G06Q 20/14* (2012.01)
*G16H 50/70* (2018.01)
(Continued)

(52) U.S. Cl.
CPC .......... *G06Q 20/14* (2013.01); *G06Q 20/102* (2013.01); *G06Q 20/227* (2013.01);
(Continued)

(58) Field of Classification Search
CPC .... G06Q 20/14; G06Q 20/102; G06Q 20/227; G06Q 30/0205; G06Q 30/04;
(Continued)

(56) References Cited

U.S. PATENT DOCUMENTS 8,239,222 B2    8/2012    eggs
2004/0034583 A1*    2/2004    Lanier .................... G06Q 40/00
705/35
(Continued)

FOREIGN PATENT DOCUMENTS

WO    WO-2007092310 A2 *    8/2007    ........... G06Q 10/107

OTHER PUBLICATIONS

Thorkildsen, How Healthcare Sharing Programs Compare to Traditional Health Insurance, Mar. 21, 2018, Kitces.com, https://www.kitces.com/blog/healthcare-sharing-program-review-chm-medicare-lhs-samaritan-health-share-plans/ (Year: 2018).*

*Primary Examiner* — Joy Chng
(74) *Attorney, Agent, or Firm* — Allen, Dyer, Doppelt + Gilchrist, PA

(57) ABSTRACT

A computing device may include a memory and a processor configured to cooperate with the memory to establish member sharing accounts for respective members of a virtual share exchange (VSE) for sharing payment of member healthcare bills across the member sharing accounts, where the members have different attributes associated therewith. For a member healthcare bill associated with a given member, the processor may calculate respective attribute scores for the other members of the VSE based upon similarities between the attributes of the other members and the attributes of the given member, rank the member sharing accounts for payment sharing of the member healthcare bill based upon the calculated attribute scores, and electronically transfer funds between the member sharing accounts for payment sharing of the member healthcare bill based upon the ranking of the member sharing accounts.

20 Claims, 8 Drawing Sheets

Related U.S. Application Data filed on May 22, 2019, provisional application No. 62/851,298, filed on May 22, 2019, provisional application No. 62/851,395, filed on May 22, 2019, provisional application No. 62/851,321, filed on May 22, 2019, provisional application No. 62/869,661, filed on Jul. 2, 2019.

(51) Int. Cl.

| | | |
|---|---|---|
| *G16H 70/20* | (2018.01) | |
| *G06Q 50/00* | (2012.01) | |
| *G06Q 30/02* | (2012.01) | |
| *G06Q 40/02* | (2012.01) | |
| *G06Q 20/10* | (2012.01) | |
| *G06Q 20/22* | (2012.01) | |
| *G06Q 40/08* | (2012.01) | |
| *G06Q 30/04* | (2012.01) | |
| *G06Q 40/04* | (2012.01) | |
| *G06Q 30/0204* | (2023.01) | |
| *G16H 40/00* | (2018.01) | |
| *G06F 3/048* | (2013.01) | |

(52) U.S. Cl.
CPC ......... *G06Q 30/0205* (2013.01); *G06Q 30/04* (2013.01); *G06Q 40/02* (2013.01); *G06Q 40/025* (2013.01); *G06Q 40/04* (2013.01); *G06Q 40/08* (2013.01); *G06Q 50/01* (2013.01); *G16H 50/70* (2018.01); *G16H 70/20* (2018.01); *G06F 3/048* (2013.01); *G16H 40/00* (2018.01)

(58) Field of Classification Search
CPC ...... G06Q 40/02; G06Q 40/025; G06Q 40/04; G06Q 40/08; G06Q 50/01; G16H 50/70; G16H 70/20; G16H 40/00; G16H 40/20; G06F 3/048
USPC .......................................................... 705/2–4
See application file for complete search history.

(56) References Cited

U.S. PATENT DOCUMENTS

| | | | |
|---|---|---|---|
| 2007/0112622 A1 | 5/2007 | Meggs | |
| 2007/0150355 A1 | 6/2007 | Meggs | |
| 2009/0030801 A1 | 1/2009 | Meggs | |
| 2010/0205096 A1* | 8/2010 | Meggs | ............... G06Q 40/08 705/44 |
| 2016/0103965 A1* | 4/2016 | Ivanoff | ............... G06Q 40/025 705/2 |
| 2018/0174153 A1* | 6/2018 | Atagun | ............ G06Q 20/40145 |

\* cited by examiner

| SOCIAL ATTRIBUTES | DATA SOURCE | MANDATORY | WEIGHT |
|---|---|---|---|
| GROUP ASSOCIATION | BANKING MODULE | YES | N/A |
| STATE OF RESIDENCY | CRM | YES | N/A |
| ZIP CODE | CRM | NO | 200 |
| MEDICAL HISTORY SIMILARITIES | ALLOCATION MODULE | NO | 100 |
| FAMILY SIZE | BILLING MODULE | NO | 100 |
| # LINKED SOCIAL MEDIA ACCOUNTS | MEMBER CENTER | NO | 50 |

FIG. 3

SOCIAL ATTRIBUTE EVALUATION: | ZIP CODE

80

BILL OWNER VALUES (81)

| ATTRIBUTE VALUE | COMPONENT 1 | COMPONENT 2 | COMPONENT 3 |
|---|---|---|---|
| 32940 | 3 | 29 | 40 |

(82)

| COMPONENT | TEXT | WEIGHT | CASCADING? | RELATIVE? |
|---|---|---|---|---|
| 1 | STATE GROUPING | 120 | TRUE | TRUE |
| 2 | REGION | 60 | TRUE | FALSE |
| 3 | AREA | 20 | TRUE | FALSE |

(83)

| MEMBER NUMBER | ATTRIBUTE VALUE | COMPONENT 1 | COMPONENT 2 | COMPONENT 3 | ATTRIBUTE SCORE |
|---|---|---|---|---|---|
| MEMBER 1 | 94632 | 9 | 46 | 32 | 48 |
| MEMBER 2 | 49825 | 4 | 98 | 25 | 108 |
| MEMBER 3 | 28284 | 2 | 82 | 84 | 108 |
| MEMBER 4 | 63320 | 6 | 33 | 20 | 84 |
| MEMBER 5 | 61673 | 6 | 16 | 73 | 84 |
| MEMBER 6 | 54567 | 5 | 45 | 67 | 96 |
| MEMBER 7 | 32930 | 3 | 29 | 30 | 180 |
| MEMBER 8 | 95663 | 9 | 56 | 63 | 48 |
| MEMBER 9 | 37641 | 3 | 76 | 41 | 120 |
| MEMBER 10 | 15820 | 1 | 58 | 20 | 96 |
| ... | | | | | ... |

FIG. 5

| ATTRIBUTE | ZIP CODE | CPT CODE | FAMILY SIZE | # SOCIAL MEDIA |
|---|---|---|---|---|
| MANDATORY? | NO | NO | NO | NO |
| MEMBER VALUE | 32940 | 29881 | 1 | 0 |
| WEIGHT | 200 | 100 | 100 | 50 |
| RELATIVE? | TRUE | FALSE | FALSE | FALSE |

| MEMBER NUMBER | ZIP CODE | CPT CODE | FAMILY SIZE | #SOCIAL MEDIA | SOCIAL PROFILE NUMBER |
|---|---|---|---|---|---|
| MEMBER 1 | 48 | 20 | 40 | 40 | 148 |
| MEMBER 2 | 108 | 60 | 10 | 20 | 198 |
| MEMBER 3 | 108 | 0 | 40 | 10 | 158 |
| MEMBER 4 | 84 | 80 | 100 | 50 | 314 |
| MEMBER 5 | 84 | 80 | 10 | 10 | 184 |
| MEMBER 6 | 96 | 10 | 80 | 20 | 206 |
| MEMBER 7 | 180 | 0 | 40 | 30 | 250 |
| MEMBER 8 | 48 | 50 | 20 | 50 | 168 |
| MEMBER 9 | 120 | 40 | 10 | 30 | 200 |
| MEMBER 10 | 96 | 0 | 40 | 0 | 136 |
| ... | | | | | |

FIG. 6

| AMOUNT NEEDED | |
|---|---|
| $ | 828.16 |

| MEMBER NUMBER | SOCIAL PROFILE NUMBER | AVAILABLE SHARE BALANCE | | AMOUNT TO DEBIT | | REMAINING FUNDS NEEDED | | NEW AVAILABLE SHARE BALANCE | |
|---|---|---|---|---|---|---|---|---|---|
| MEMBER 4 | 314 | $ | 402.62 | $ | 402.62 | $ | 425.54 | $ | - |
| MEMBER 7 | 250 | $ | 50.84 | $ | 50.84 | $ | 374.70 | $ | - |
| MEMBER 6 | 206 | $ | 200.90 | $ | 200.90 | $ | 173.80 | $ | - |
| MEMBER 9 | 200 | $ | 71.34 | $ | 71.34 | $ | 102.46 | $ | - |
| MEMBER 2 | 198 | $ | 596.14 | $ | 102.46 | $ | - | $ | 493.68 |
| MEMBER 5 | 184 | $ | 478.06 | $ | - | $ | - | $ | 478.06 |
| MEMBER 8 | 168 | $ | 410.00 | $ | - | $ | - | $ | 410.00 |
| MEMBER 3 | 158 | $ | 660.92 | $ | - | $ | - | $ | 660.92 |
| MEMBER 1 | 148 | $ | 437.88 | $ | - | $ | - | $ | 437.88 |
| MEMBER 10 | 136 | $ | 323.90 | $ | - | $ | - | $ | 323.90 |
| ... | | ... | | ... | | ... | | ... | |

FIG. 7

COMPUTING SYSTEM FOR SHARING NETWORKS PROVIDING PAYMENT ALLOCATION BASED UPON ATTRIBUTE SCORING AND RELATED METHODS

CROSS-REFERENCE TO RELATED APPLICATIONS

This application claims the benefit of provisional application Nos. 62/851,282; 62/851,279; 62/851,298; 62/851,395; 62/851,321 filed May 22, 2019, and provisional application No. 62/869,661 filed Jul. 2, 2019, all of which are hereby incorporated herein in their entireties by reference.

TECHNICAL FIELD

The present invention relates generally to computing systems and, more particularly, to computer infrastructures that provide for implementation of Virtual Share Exchange (VSE) platforms.

BACKGROUND

In recent years, health care expense sharing has emerged as a "decentralized" approach to financing and reserving for health care costs. As a "non-insurance" alternative, health care sharing is not subject to typical insurance regulations. Individual participants are legally and ultimately responsible for their own medical bills. However, participants in health care sharing networks willingly and consistently share from their own personal funds to pay each other's medical bills.

Some health care sharing networks implement a technology framework often called a Virtual Share Exchange (VSE). The VSE may include a collection of virtual account management, billing, and payment technologies that form a comprehensive and transparent health care sharing process. The VSE model enables health care sharing networks to facilitate sharing programs on a P2P (or member-to-member) basis to help provide compliance with applicable safe harbor exemptions to insurance regulations.

VSE platforms have enabled healthcare sharing networks to rapidly grow and scale similar to institutional computer network models, like health insurance. Modern VSE platforms have become advanced Fintech applications that integrate all the stakeholders and financial processes that are necessary to facilitate member-to-member sharing via computer networking and electronic payment infrastructure.

SUMMARY

A computing device may include a memory and a processor configured to cooperate with the memory to establish member sharing accounts for respective members of a virtual share exchange (VSE) for sharing payment of member healthcare bills across the member sharing accounts, where the members have different attributes associated therewith. For a member healthcare bill associated with a given member, the processor may calculate respective attribute scores for the other members of the VSE based upon similarities between the attributes of the other members and the attributes of the given member, rank the member sharing accounts for payment sharing of the member healthcare bill based upon the calculated attribute scores, and electronically transfer funds between the member sharing accounts for payment sharing of the member healthcare bill based upon the ranking of the member sharing accounts.

The processor may be further configured to aggregate the attribute scores into respective profile scores for each member, and rank the member sharing accounts for payment sharing based upon the profile scores. In some example configurations, at least one of the attributes may comprise a mandatory attribute, and the processor may be configured to exclude from the ranking member sharing accounts of members with the mandatory attribute different than the mandatory attribute of the given member.

In an example embodiment, one of the attributes may comprise zip codes associated with the members, and the processor may be configured to calculate zip code attribute scores for the other members based upon matching of at least a portion of their zip codes with a zip code of the given member. More particularly, the processor may be further configured to calculate respective state grouping, region, and area attribute scores for the other members from their zip codes based upon matches with a state grouping, region, and area associated with the zip code of the given member, for example.

In accordance with another example, one of the attributes comprises medical conditions, and the processor may be configured to calculate respective medical condition attribute scores based upon matching medical conditions of the other members with a medical condition of the given member. For example, the processor may be configured to determine the medical conditions of the members from Current Procedural Terminology (CPT) codes within at least one of a member medical history profile, and within the member medical bills submitted to the virtual share exchange.

In still another example, one of the attributes may comprise family compositions of the members, and the processor may be configured to calculate family composition attribute scores based upon matching of family compositions of the other members with a family composition of the given member. By way of example, the processor may be further configured to calculate respective number of participants, gender, and age attribute scores for the other members based upon matches with a number of participants, genders, and ages associated with the family of the given member. In accordance with another example embodiment, one of the attributes may comprise social media interests, and the processor may be configured to calculate social media interest attribute scores based upon matching of social media interests of the other members with social media interests of the given member for member social media accounts linked to the member sharing accounts.

A related method may include establishing, at a server, member sharing accounts for respective members of a VSE for sharing payment of member healthcare bills across the member sharing accounts, where the members have different attributes associated therewith. The method may further include, for a member healthcare bill associated with a given member, calculating respective attribute scores at the server for the other members of the VSE based upon similarities between the attributes of the other members and the attributes of the given member. The method may also include ranking, at the server, the member sharing accounts for payment sharing of the member healthcare bill based upon the calculated attribute scores, and electronically transferring funds at the server from the member sharing accounts for payment sharing of the member healthcare bill based upon the ranking of the member sharing accounts.

A related non-transitory computer-readable medium may have computer-executable instructions for causing a computing device to perform steps including establishing member sharing accounts for respective members of a VSE for sharing payment of member healthcare bills across the member sharing accounts, where the members have different attributes associated therewith. For a member healthcare bill associated with a given member, respective attribute scores may be calculated for the other members of the VSE based upon similarities between the attributes of the other members and the attributes of the given member. The steps may further include ranking the member sharing accounts for payment sharing of the member healthcare bill based upon the calculated attribute scores, and electronically transferring funds between the member sharing accounts for payment sharing of the member healthcare bill based upon the ranking of the member sharing accounts.

BRIEF DESCRIPTION OF THE DRAWINGS

FIG. 3 is a table illustrating an example VSE sharing profile based upon member attributes which may be used by the computing device of FIG. 1.

FIG. 5 is a table illustrating an example approach for using the component attributes from FIG. 4 to generate member attribute scores.

FIG. 6 is a table illustrating an example approach for generating a member profile score based upon the component attributes from FIG. 5.

FIG. 7 is a table illustrating ranking of member sharing accounts from the example of FIG. 6 based upon the member profile scores for determining bill contributors and allocation.

BRIEF DESCRIPTION OF THE DRAWINGS

Example embodiments will now be described more fully hereinafter with reference to the accompanying drawings, in which the example embodiments are shown. The embodiments may, however, be implemented in many different forms and should not be construed as limited to the specific examples set forth herein. Rather, these embodiments are provided so that this disclosure will be thorough and complete. Like numbers refer to like elements throughout.

Figure 1:
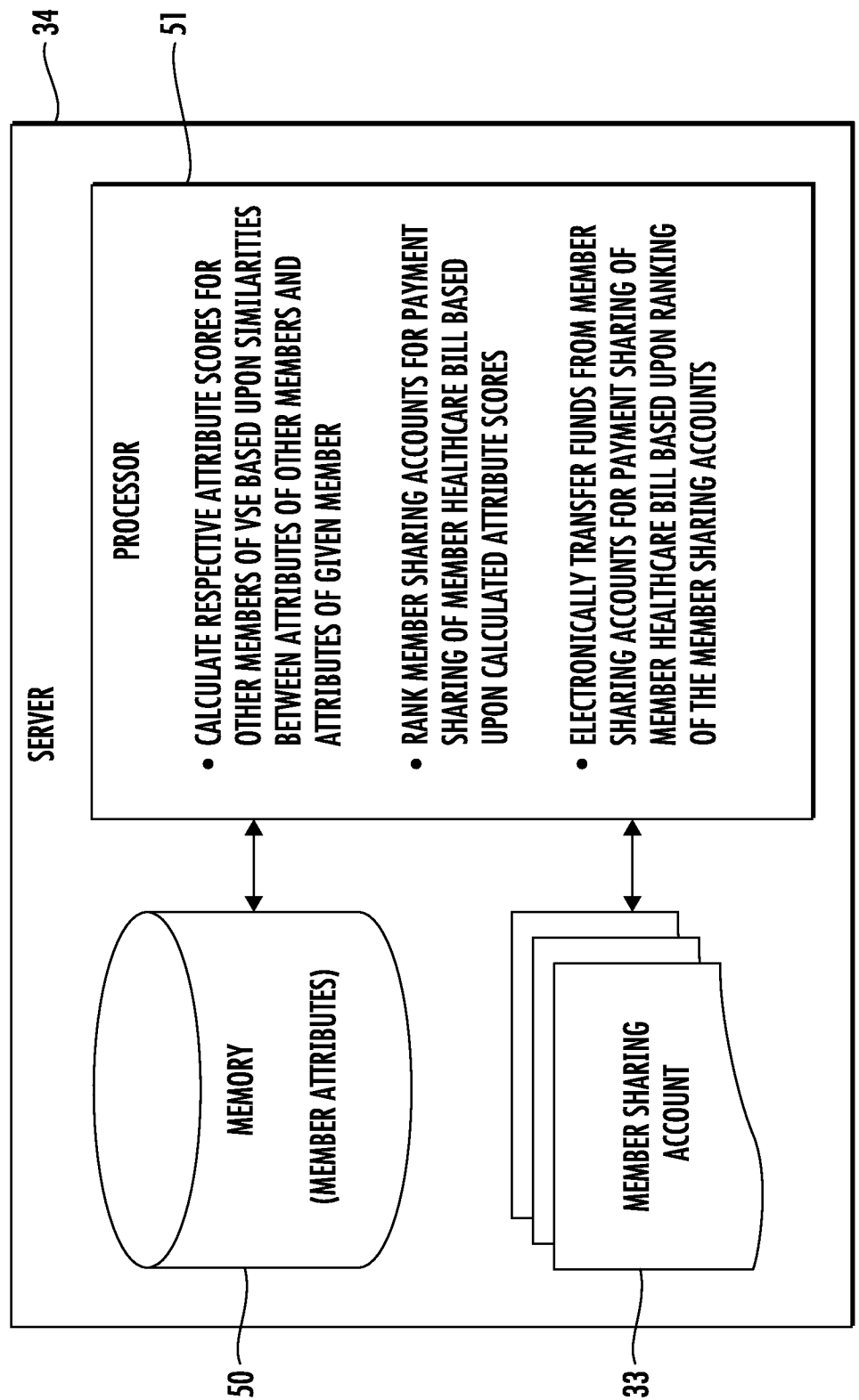
FIG. 1 is a schematic block diagram of a computing device for implementing a virtual share exchange (VSE) computing platform in an example embodiment.
Figure 2:
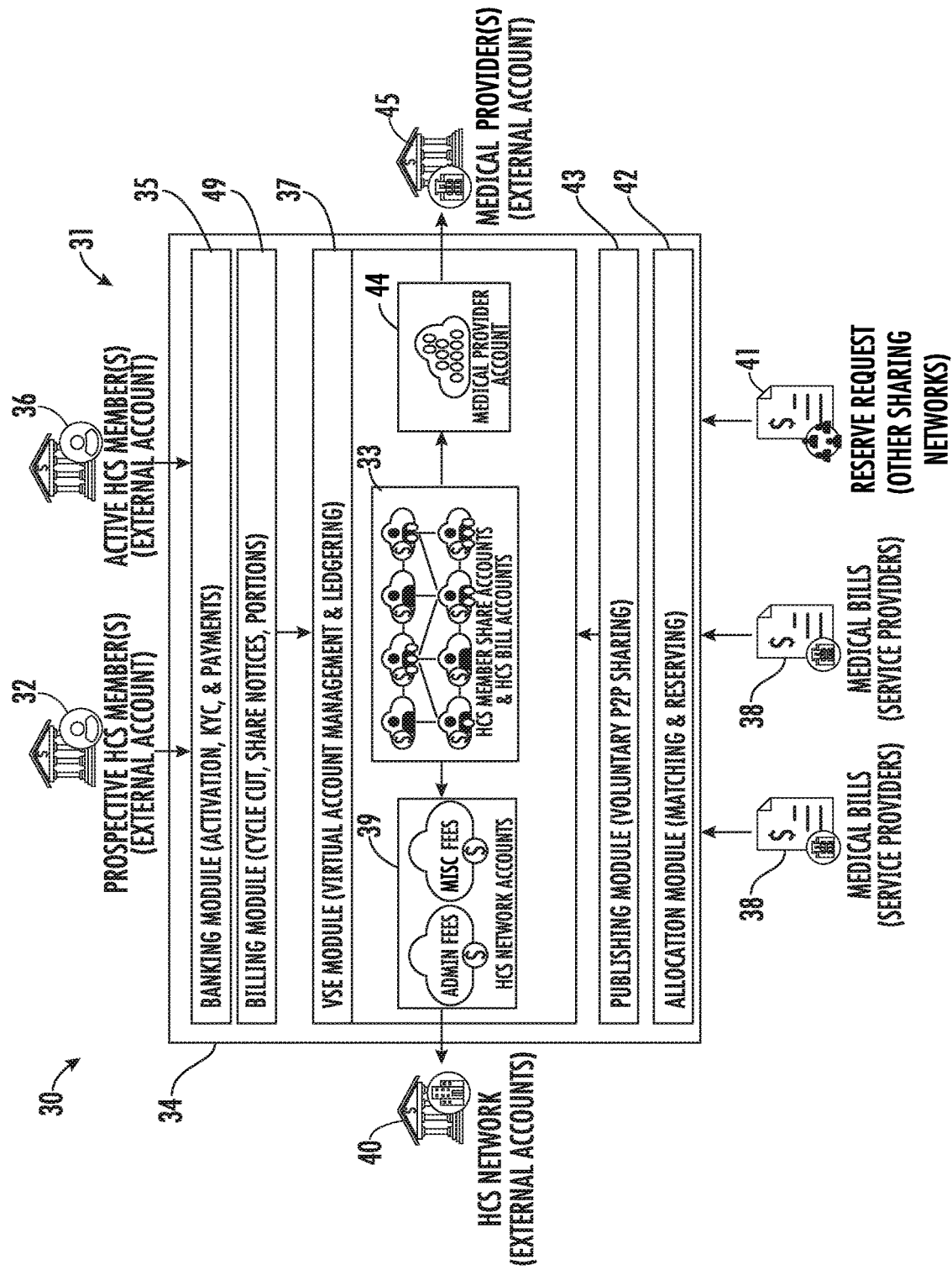
FIG. 2 is a schematic block diagram of an example computing system including the computing device of FIG. 1 providing a VSE computing platform for a healthcare sharing network.

Referring initially to FIGS. 1-2, a computing system 30 and associated computing device (e.g., server) 34 which provide for payment sharing within a virtual share exchange (VSE) platform 31 based upon similarities of member attributes are now described. The computing device 34 illustratively includes a memory 50 and a processor 51 configured to cooperate with the memory to perform the operations or steps described further below. By way of background, individuals joining forces as a group to achieve certain benefits and advantages is common in many facets of our everyday life. The power of groups is largely evident in the pooling practice found in the traditional insurance model. By pooling their resources through a centralized insurance company or common fund, groups are able to finance, reserve, and pay the expenses associated with the type of insurance risk. Without being able to rely on the insurance company and its practice of pooling funds, the individuals would be left to bear the cost and risk of a catastrophic loss by themselves.

Historically, traditional insurance companies were largely successful at helping groups of individuals finance and reserve for their expenses and catastrophic risk. By collecting and pooling both the risk and the resources of individuals into centralized group fund, traditional insurance coverage and the benefits obtained therefrom were made more affordable. In the past, the efficiency of pooling and reserving resources in a centralized fund enabled insurance companies to not only provide affordable coverage, but to capture a profit or bounty for pooling those resources into a central fund. Resources that are collected and pooled into the centralized fund are called "premiums", which is derived from the Latin word "praemium" and defined as a "reward, profit or bounty for a specified act". Thus, insurance companies were able to generate significant profit by extracting a "premium" from groups of individuals who were unable to pool resources to finance and reserve for their individual risk of catastrophic loss and costs.

Traditionally, the affordability of insurance coverage was predicated upon the overall wellness of the group and their consumption of services. For example, in healthcare, some members' need for medical services could be little more than annual checkups, while other individuals might need to access and consume services much more extensively. It is the latter group that has a greater effect on the overall costs of the group and the subsequent premiums collected. For those that do not frequently draw upon the centralized fund's resources, being lumped with the more extensive users is unfavorable. On the flip side, those who consume a larger share of the benefits may enjoy lower premiums because the individuals that consume little are subsidizing the expense of frequent consumers. In the past, insurance companies would respond to individuals who draw disproportionally on the centralized fund by raising their premiums to maintain group equity and ensure company profits.

With respect to financing and reserving for health care, the average consumer would not be able to afford much more than the very basic of health care services if the pooling of resources was not available through insurance. In fact, based upon current rates being charged by the medical industry, cutting edge or life-saving surgeries, drugs and treatments would be difficult, if not, impossible, for the average consumer to obtain.

However, in recent years the affordability and profitability of the traditional insurance model has been degraded by the enactment of government regulations. New laws and regulations have all but eliminated an insurance company's ability to segment groups of healthy individuals into centralized funds, or plans, that price premiums according to the group's health and draw on resources. Similarly, new regulations have mandated that all centralized funds, or plans, cover new and more extensive medical services not historically offered by health insurance companies. As a result, health insurance companies have been greatly limited in their ability to offer affordable coverage that is reflective of the health condition and medical usage of individual participants, as well offer affordable plans that provide access to the medical services that participants actually desire, versus services the government mandates.

Another disadvantage of the health insurance model and the associated regulations is that individuals of the centralized fund and plan can lead unhealthy or "at risk" lifestyles such as high-risk diets, low exercise, smoking, excessive alcohol intake and the use of illicit drugs, all without consequence. By engaging in such lifestyles, these individuals increase their likelihood of drawing on the resources and benefits of the centralized fund. The more these "high-risk" individuals are allowed to make choices and lead lives without consequences, the more likely that costs and premiums increase for everyone in the fund.

An additional disadvantage of the centralized insurance model is that the plan benefits are distributed to individuals of the group in such a way that no other individual participating in the plan has any real sense of what types of benefits or services are being paid for by the insurance company. The centralized insurance model provides no visibility into the size of the fund, the number of participating individuals, the size of available reserves, the flows of money, or profits pocketed by the insurance company. Thus, participating individuals are unaware of the financial health and wellness of the fund. This lack of transparency also makes individuals feel less responsible for their lifestyle choices that increase their draw of resources, as well as less connected and accountable to their fellow participants who are paying their bills.

The structural inefficiencies, inherent in the design of the centralized health insurance model, have been recently exposed by the new government mandates and regulations in health care. It has caused a rapid and unsustainable rise in premiums and insurance costs. Thus, the centralized health insurance model has become unaffordable and subsequently obsolete. And while the changes have been focused exclusively on healthcare, the aforementioned problems similarly persist in the other insurance markets.

As a result, consumers have sought out new and more innovative ways to organize themselves into groups that leverage the strength of their combined resources to finance and reserve for their health care costs. Unlike the centralized insurance model, consumers are turning to decentralized network models that are enabled by technologies that replace the pooling functions of traditional insurance companies.

In recent years, health care sharing has emerged as the most popular "decentralized" approach to financing and reserving for health care costs. As a "non-insurance" concept, health care sharing is not encumbered by insurance regulations. Individual participants are legally and ultimately responsible for their own medical bills. However, participants in health care sharing networks willingly and consistently share from their own personal funds to pay each other's medical bills. Health care sharing networks have been in existence since the early 1980s, but in recent years have grown to become a significant alternative to the centralized insurance model. Today, health care sharing networks enjoy safe harbor exemptions in U.S. health care laws and more than 30 states. Participants of health care sharing networks are sharing billions of dollars worth of medical bills on an annual basis. Free from insurance regulations, health care sharing networks can design and implement programs that are more efficient and affordable than insurance, as well as hold participants more accountable to each other.

As noted above, some health care sharing networks implement a technology framework often called a Virtual Share Exchange or VSE. The VSE platform 31 set forth herein may include a collection of computing hardware (e.g., servers or other computing devices including microprocessors and associated memory with non-transitory computer readable instructions) to implement virtual account management, billing, and payment modules that form a comprehensive and transparent health care sharing process. The VSE model enables health care sharing networks to facilitate sharing programs on a P2P (or member-to-member) basis to help ensure that these sharing networks refrain from the practice of insurance, and remain in compliance with the safe harbor exemptions of insurance rules/regulations.

Moreover, contemporary VSE platforms 31 have enabled healthcare sharing networks to rapidly grow and scale their networks by leveraging social trends towards the democratization of centralized institutional business models, like health insurance. Modern VSE platforms 31 have become advanced Fintech applications that integrate all the stakeholders and financial processes that facilitate member-to-member sharing, which will now be discussed further with reference to FIG. 2.

Prospective members 32 are consumers who are applying for membership into the sharing network and its community. In order to complete their application for membership, prospective members 32 set-up and activate their share account 33 through a computing device(s) 34, such as a server. In an example embodiment, the computing device 34 may be part of a cloud computing architecture, although other configurations may be used in different embodiments. Share or sharing accounts 33 are activated through a graphical user interface or GUI (often called the Application Center or Activation Center) to access account activation services within a banking module 35 of the computing device 34.

Active members 36 are consumers who have been accepted and are active in the sharing network and associated community. Active members 36 make monthly deposits (called monthly share amounts) electronically into their share account 33 that is held within a VSE/for the benefit of (FBO) module 37 of the computing device 34. To pay (or deposit) their monthly share amount into their share account 33, members 36 access services within the banking module 35 through a graphical user interface, as noted above. The banking module 35 provides services that enable members 36 to link their share account 33 to an external payment method and initiate recurring monthly transactions.

The banking module 35 may be implemented as a cloud-based application that enables both prospective members 32 and active members 36 to activate and manage their participation in the sharing network's program through a financial account (called a share account 33) that the member owns and controls. The banking module 35 enables members 36 to link an external bank account to their share account 33, to fund their share account per the terms of the sharing network, and to manage banking and regulatory compliance.

The billing module 49 may be implemented as a cloud-based application that calculates monthly share prices and creates the monthly share notices for the sharing network. Moreover, the billing module bills, publishes and collects the monthly share notice per the terms of the sharing network.

The VSE/FBO module 37 may also be implemented as a cloud based virtual account management and ledgering system that enables the sharing network to facilitate the member-to-member sharing and payment of member bills. The VSE/FBO module 37 enables member-to-member sharing through virtual accounts 33 that are owned and individually controlled by the members 36 and not the sharing network, as well as to house those virtual accounts in a single FBO account held by a financial institution "for the benefit of" the member 36.

The member share accounts 33 are member owned and controlled virtual accounts maintained by the VSE/FBO module 37, and are required for members 36 to participate in the sharing network. The share accounts 33 enable the sharing network to build distributed reserves in accounts that are owned and controlled by its members 36, and facilitate member-to-member sharing through those accounts.

Sharing network fee accounts 39 are virtual accounts maintained by the VSE/FBO module 37 that are owned and controlled by the sharing network and used to comply with any potential regulatory constraints. The fee accounts 39 help segregate "member owned" funds that are held in share accounts 33 and used for sharing from "network owned" funds, which are operating fees that are billed and collected as a part of a monthly share notice.

Sharing network external accounts 40 are external bank accounts that are owned and controlled by the sharing network and are linked to a specific sharing network fee account 39 that resides in the VSE/FBO module 37. As operating fees are collected through the payment by members 36 of monthly share notices, sharing networks are able to access those funds by transferring them out of the sharing network fee account 39 to its linked external account 40. The sharing network external accounts 40 allow for withdrawing operating funds out of the VSE/FBO module 37.

The member bills 38 are invoices billed by a member's service provider that have been received by the sharing network. The member bills 38 are to be shared by the members of the sharing network per the network's guidelines.

A sharing reserve request 41 represents a member bill from another sharing network that is participating in a federation or collaboration of sharing networks who have agreed to share in each other's member bills per the terms of a shared reserve agreement. Further details regarding sharing reserve requests are set forth in co-pending U.S. application Ser. No. 15/931,786 filed May 14, 2020, which is hereby incorporated herein in its entirety by reference.

An allocation module 42 may be implemented as a cloud-based bill matching and allocation service enabling sharing networks to facilitate bill sharing, help ensure regulatory compliance, and to generate more meaningful sharing transactions. The allocation module 42 may be used to match and allocate bills on a member-to-member basis, and to draw down distributed bills in a way that is equitable to all members 36.

A publishing module 43 may be implemented as a cloud-based notification and sharing service for initiating member-to-member (P2P) account transfers. The publishing module 43 notifies members 36 as to whose bill they have been matched to, and how much of their available share account 33 balance has been allocated as a contribution to the payment that member's bill, as well as to provide each matched member with the means to voluntarily share (agree) in the payment of that bill.

The provider account 44 is a virtual account within the VSE module 37 that is owned and managed by individual service providers, or a single virtual "settlement" account that aggregates funds for multiple payments made to multiple service providers, or some combination of both. The provider account(s) 44 segregate funds that have been shared and collected for the payment of a bill 38 or 41, and to make those funds available to the appropriate service provider.

An external provider account 45 is a linked external account owned and managed by an individual service provider for transferring funds out of the VSE/FBO module 37 or linked external account owned and managed by a payment processor for transferring multiple payments to be made to multiple service providers. More particularly, the provider external accounts 45 allow for withdrawing bill 38, 41 payments out of the VSE/FBO module 37.

In recent years, technology innovations and platforms like VSEs have played an enabling role in social trends that advocate business models that democratize the hold of entrenched centralized institutions. This has been the case in the rapid growth of sharing networks, especially healthcare sharing networks that replace the need for comparatively expensive health insurance. Additionally, as payment sharing becomes more commonplace amongst consumers, many may be drawn to the concepts whereby their monthly healthcare contributions are shared exclusively with those to which there is an inherent synergy and common loyalties.

People that have decided to seek healthcare provisions outside of health insurance networks commonly seek to join a community where they have shared ideological, philosophical, or religious beliefs. Further, the very definition of a health care sharing within the federal regulatory statutes obliges members to "share a common set of ethical or religious beliefs." As mentioned previously, the proverbial backbone by which all health care sharing networks exist is that members with medical expenses (referred to hereinafter as a "bill owner"), effectively, inform, broadcast, or publish their healthcare expenses to the other share network members in hopes that the other members will financially contribute to those published expenses.

As such, some sharing networks may benefit if their members share additional meaningful similarities beyond the obligatorily shared "common set of ethical or religious beliefs." By pairing financial contributors (referred to hereinafter as a "bill contributor") to the bill owners within their share network that share additional affinities (referred to hereinafter as a "attributes") may uniquely produce the most meaningful sharing opportunities possible and may create a deeper interest of bill contributors to continue to participate in the sharing network by financially contributing to the healthcare needs of others.

Generally speaking, to accomplish these sharing interactions, health care sharing networks (or other sharing networks) may utilize the VSE platform 31 to segment the member 36 population by an array of attributes. Share networks may initially seek to match bill owners and bill contributors by using broader attributes such as a defined group association (e.g., employer, church, denomination, association, ethnic group) or even state residency. However, the VSE platform 31 may advantageously find meaningful commonality amongst its share network members by programmatically parsing and comparing datasets from a myriad of applications, services, and databases integrated with or even within the VSE to generate a sharing profile number or score. A higher sharing profile number may indicate significant social similarities between the bill contributor and the bill owner, whereas a lower sharing profile number predicts lesser similarities than of those bill contributors and bill owners with a higher score. The sharing profile number may then be used to determine the ranking or order in which available share dollars within member share accounts are drawn from the bill contributor accounts, allocating first from bill contributors with the highest social profile number or score when related to the bill owner of a particular medical bill 38 or, when applicable, a reserve request 41 from a distinct share network.

In the illustrated example, the VSE platform 31 is configured to aggregate, compare, contrast, interpret, and/or parse data from disparate internal or external data sources for the purpose of routinely and automatically determining the members with an available share balance in their share account 33 best suited to serve as a bill contributor for a given medical bill 38 or reserve agreement 41.

A sharing network 40 using the VSE platform 31 may have internal business rules or even regulatory constraints that require the sharing network to have specific parameters in the pairing of a bill owner and a bill contributor. The sharing network 40 inputs those specificities and preferences into a VSE social sharing profile 60 (FIG. 3) including the VSE's social attributes (section 61). The VSE social sharing profile may be implemented in a database stored within a memory 50 at the computing device 34 (e.g., server). Sharing networks 40 may desire or may be obligated to have a central, universally shared set of beliefs or values within the share network, as discussed above.

The VSE platform 31 may advantageously satisfy this obligation by configuring a "group association" (section 62) for the members 36 within the share network 40. Other example applications of a group association may include employers, university-affiliated individuals, or any large group that desires to have sharing exclusively maintained between bill owners and bill contributors who share that specific social attribute. Similarly, some share networks 40 may not have a specific group association that is the social attribute that establishes the exclusivity between members, but rather the state of residency is shared between the bill owner and bill contributor. To that end, the VSE platform 31 may allow for share networks 40 to determine if social attributes are mandatory or simply preferential (section 63).

To allow for share networks 40 to have the most meaningful social attributes to be considered within their VSE social sharing profile, the VSE platform 31 may use the social sharing profile to programmatically parse and/or compare datasets from a myriad of data sources (section 64) including applications, services, and databases integrated with or even within the VSE platform 31. Moreover, the sharing networks 40 may integrate or otherwise acquire data from a marketing reference database, a Customer Relationship Management (CRM) tool, social media applications members 36 may have integrated with their share network, and publicly available datasets, for example. Furthermore, such information may be provided by members 36 when joining while they were perspective members 32, during the course of their membership as active members 36, while interacting with the banking module 35 and/or billing module 49, within member bills 38 or allocation module 42, and within reserve requests 41. These data points are readily available internally within the VSE platform 31 for making sharing attribute determinations and calculations.

The VSE social sharing profile 60 identifies the desired social attributes for a sharing network 40. Those social attributes themselves have properties that may need further configuration within the VSE platform 31. In order for a social attribute to be considered, the data source containing the values of those social attributes will integrate in some manner with the VSE platform 31, such as through an application programming interface (API), for example. The VSE platform 31 allows social attributes that are core to the sharing network 40 to be designated as mandatory social attributes (section 63) in the selection of bill contributors for a particular medical bill 38 or reserve request 41. The VSE social sharing profile 60 may also allow the share network 40 to have social attributes signifying varying degrees of relevance to the share network by adjusting the weight (section 65) of a given social attribute. For social attributes that have greater significance to the share network, a higher weight may be given. Similarly, if a social attribute is less significant to the share network, it may be given a lower weight.

In the example of FIG. 3, the share network 40 has elected to have two (2) mandatory social attributes, group association and state of residency (section 63). Therefore, as the VSE allocation module 42 queries the member share accounts 33, only active members 36 that have identical group association and state of residency values to that of the specific bill owner are considered in order to determine potential bill contributors. That is, the members 36 that do not have identical group associations and states of residency will have their accounts 33 excluded from the scoring/ranking of accounts from which the bill contributors are selected. The example in FIG. 3 also indicates that the share network 40 has six (6) social attributes (section 61) of group association, state of residency, zip code, medical history similarities, family size, and the number of social media accounts linked to the sharing network 40.

The illustrated example shows that the attributes come from distinct data sources (section 64) including the billing module 49, CRM, allocation module 42, and member center (i.e., from prospective members 32). Also, the share network 40 has four (4) non-mandatory social attributes (section 66) with various weights assigned thereto (section 65), which in the present example are 200 (Zip Code), 100 (Medical history Similarities and Family Size), and 50 (# Linked Social Media Accounts).

Moreover, the social attributes that are mandatory include the group association and state of residency (section 62). The group association data is located in the banking module 35 as it information most commonly conveyed during the financial transaction with the share network. The State of Residency information about a Member is found most commonly in the share network's CRM system. Mandatory social attributes within the VSE social sharing profile may act as a type of binary filter for share networks in that there is either an absolute match or not, and therefore there is no weight. Stated alternatively, by not having an identical value on mandatory social attributes (section 63) with the bill owner, prospective bill contributors are prohibited from actually participating in paying towards a medical bill 38 or reserve request 41. Therefore, mandatory social attributes (section 63) have no weight (section 65) in the process as the bill owner and all prospective bill contributors have precisely the same value. The weights assigned to the different attributes may also be considered as attribute scores, which may be aggregated or combined (e.g., summed) to create a Social Profile Number (SPN) or score (see table 90, FIG. 6) to rank bill contributors for payment sharing for respective bills 38 or share requests.

Use of weighting helps the VSE platform 31 automate increasing the likelihood that bill contributors will match to bill owners who have greater meaningful social similarities beyond the mandatory group association and state of residencies. Evaluating and aggregating the weight of each social attribute on a prospective bill contributor produces an SPN for that bill contributor (FIG. 6, section 100). By having a higher SPN, the bill contributor is more likely to have greater meaningful social similarities beyond the mandatory group association and state of residencies.

A sharing network 40 may have broad social attributes listed in VSE's Social Sharing Profile. In the example of FIG. 3, the non-mandatory attributes (section 66) include "Zip Code", "Medical History Similarities", "Family Size", and "Linked Social Media Accounts". Each one of those social attributes may within themselves have varying degrees of relevance to the share network 40 in selecting the most meaningful sharing opportunity for the bill contributor. In an example implementation, each of those social attributes may have the following components.

Figure 4:
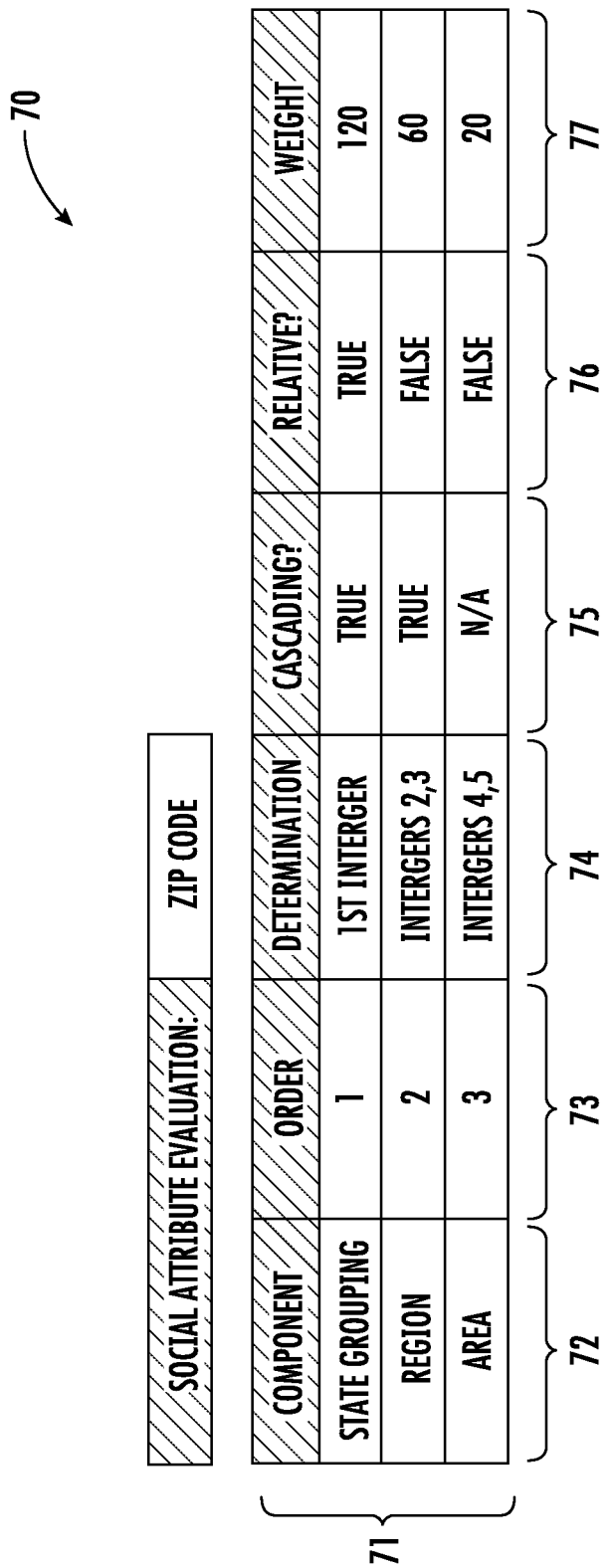
FIG. 4 is a table illustrating an example approach for parsing a member attribute from the table of FIG. 3 into further components attributes.

With respect to zip codes, as shown in the table 70 of FIG. 4, U.S. zip codes are broken down into three components, namely state grouping, region, and area (sections 71-72). The specificity of how components may operate within the social attributing process of the VSE platform 31 is discussed further below with respect to FIG. 5.

With respect to medical history similarities, the VSE platform 31 may determine individuals who have historically, or are actively experiencing, similar medical ailments, as they may have a stronger bond in sharing medical expenses. The share network 40 generally may ask for a medical history from prospective members 32, and the VSE platform 31 will be aware of any new ailments that are listed in member bills 38 (or reserve requests 41). By evaluating relevant Current Procedural Terminology (CPT) codes (see FIG. 6, section 97) for both the bill owner and potential bill contributors, the VSE platform 31 is able to still protect all applicable privacy concerns as there is no mechanism to expose the creation of the sharing profile number or the variables utilized.

With respect to family size, the VSE platform 31 may determine individuals who have similar family compositions within the membership (section 93), including the number of participants, gender, ages, etc. Here again, similarities in this attributes may indicate a better match between members for sharing medical expenses. By utilizing data already available within the VSE platform 31, the system 30 is still able to still protect all applicable privacy concerns as there is no mechanism to expose the creation of the sharing profile number or the variables utilized.

With respect to linked social accounts, the VSE platform 31 may determine members 36 who have similar social media interests integrated with their member center (section 94), which again may provide a stronger bond between members 36 for sharing medical expenses. By utilizing data already available within the VSE platform 31, the share network 40 is still able to still protect all applicable privacy concerns as there is no mechanism to expose the creation of the sharing profile number or the variables utilized.

As noted above, each social attribute that is not mandatory may have some type of weight associated with it to indicate varying degrees of relevance as directed by the share network 40. In the example of FIG. 3, by having "Zip Code" contain a value of 200 for the weight means that the share network 40 deems that attribute four (4) times more valuable than "Linked Social Media Accounts", as it has a weight of 50 (section 65). Zip code is also two times (2) more valuable than either "Medical History Similarities" or "Family Size" as they both have weights of 100. By each having a Weight of 100, "Medical History Similarities" and "Family Size" have equal relevance to the share network. It should be noted that other weighting values or numbering scales may be used in different embodiments.

Referring to the table 80 of FIG. 5 and section 80-83, to compute the SPN for a bill contributor, an attribute score (section 83) may be computed for each non-mandatory attribute. Determining the attribute score may require parsing the attribute into components. As noted above, FIG. 4 provides an example of taking a social attribute (Zip Code) and parsing it into components (section 72) for the purpose of gaining specificity in ascertaining more meaningful sharing opportunities. Components may themselves have properties such as a "Order" (section 73), "Determination" (section 74), "Cascading" (section 75), "Relative" (section 76), and "Weight" (section 77).

In the example provided in FIG. 3, the social attribute "Zip Code" is being further divided into three (3) components, namely "State Grouping", "Region", and "Area". In the United States, Zip Codes have five integers. The determination (section 74) is a unique way to calculate the value of the corresponding component. In the present example, the determination of the "State Grouping" component is the first integer of the "Zip Code". The determination of the "Region" is the second and third integers of the "Zip Code", while the determination for the third Component "Area" is the fourth and fifth integers of the "Zip Code."

Furthermore, cascading components (section 75) are components in which preceding components, or components with a lower value order integer (section 73) establish a parent/child data dependency upon the successive components, or components with a larger value "Order" integer. Referring to section 81 of FIG. 5, the attribute zip code is being evaluated and the example bill owner has a zip code value of "32940." Because the component ("State Grouping") with the lowest value "Order" integer ("1") (section 73) is cascading, the VSE platform 31 will couple the next component in succession based upon the "Order" values. Again referring to section 81 of FIG. 5, the bill owner value for the attribute is "32940." The component with the lowest order ("State Grouping") integer ("1") has a determination ("1st Integer") that dictates the value for Component 1 is to be "3". The component with the second lowest order ("Region") integer ("2") has a determination ("Integers 2,3") that dictates the value for Component 2 is to be "29". The component with the third lowest Order ("Area") integer ("3") has a determination ("Integers 4,5") that dictates the value for Component 2 is to be "40". Because of the cascading component or Component 1, potential bill contributors with zip codes values where the Integers 1,2, and 3 are "329" would be awarded a higher attribute score (section 83) then, say, a potential bill contributor with a zip code value where the Integers 1,2,3, are "229" or "429".

In the table 70, the social attribute "Zip Code" is being subdivided into three (3) components, namely "State Grouping", "Region", and "Area." Two (2) of these components are not relative ("Region" and "Area") where one (1) component is relative ("State Grouping"). Relative components (section 76) allow for non-exact match values to generate a partial contribution to the attribute score (section 83) proportionate to the absolute value of the difference between the value of the bill owner and the value of the prospective bill contributor. If a component is not relative, exact matches are the only values that contribute to the attribute score.

When referring to the example provided in FIG. 3, the social attribute "Zip Code" is being evaluated into three (3) components, namely "State Grouping", "Region", and "Area." The weight of the component (section 77) uniquely indicates how a component contributes positively towards an attribute score. The value may express the maximum allowance towards the attribute score. A high value may signify a higher degree of relevance to the share network 40, whereas a lower value may signify less relevance to the share network. The "State Grouping" component has a Weight value of "120", the "Region" Component "60", and the "Area" component "20".

The example provided in FIG. 5 represents the calculation of an attribute score for the Zip Code attribute by the processor 51 (FIG. 1). In order to create an attribute score, the processor 51 may identify the specific attribute being evaluated, the values of that attribute for the bill owner and potential bill contributors, and the components with their respective properties.

In section 81 (FIG. 5), the value of the Zip Code for the bill owner is 32940 and may be parsed into the following components: Component 1 ("3"); Component 2 ("29"); and Component 3 ("40). Section 82 summarizes the definitions and examples from FIG. 4. Further, the example provided in section 82 illustrates how the weight for an attribute may be dispersed amongst the components.

In section 83 a summary is provided of ten (10) prospective bill contributors, their respective attribute value (Zip Code) and then how those values are parsed into their corresponding components. As seen in section 82, the attribute score evaluates Component 1 with the greatest weight (120), and since it is a relative component each prospective bill contributor (section 83) will be given a score for that component that is proportionate to the absolute value of the difference between the value of the bill owner and the value of the prospective bill contributor. Any prospective bill contributor who has a matching value for Component 1 ("State Grouping") to that of the Bill Owner ("3") is given the full Weight ("120") of the component towards their attribute score. Only one (2) of the prospective bill contributors ("Member 7" and "Member 9") has a perfect match.

Furthermore, considering the component is indeed relative, each prospective bill contributor with a valid value in Component 1 will receive some type of non-zero scoring for this attribute. Additionally, two (2) instances appear in the example data that may receive the same relative scoring for Component 1 as the difference between their respective values and that of the bill owner have the same absolute value ("Member 2" and "Member 3"). The relative score may merit roughly ninety percent (90%) of the weight (120) for Component 1, and therefore the attribute score will reflect as much accordingly (108). Components 2 ("Region") and 3 ("Area") are not relative, so only exact matches to the respective values of the bill owner ("29" and "40") earn a non-zero value for the attribute score.

Additionally in the example, two (2) members ("Member 7" and "Member 9") both have exact matches for Component 1 ("3"). While both are thereby given the corresponding weight ("120") towards their attribute score, only one (1) has an additional exact match in either of Component 2 or Component 3 ("Member 7"). Therefore the prospective bill contributor ("Member 7") has the additional weight ("60") of the matching component ("Component 2") added to their attribute score (180).

Referring now to the table 90 of FIG. 6 and section 91-101, the illustrated shows how the processor 51 computes the social profile number or score (section 100) by aggregating the attribute scores across all potential bill contributors and attributes (section 101). The VSE platform 31 may summarize the particular bill owner values (section 95) for the respective attributes. In the illustrated example, the Zip Code attribute (section 91) is not a mandatory attribute, the bill owner's value is known ("32940") and the attribute weight ("200") is relative. Attribute 2 ("CPT Code", section 92) is not mandatory for a known value ("29881") and the attribute weight ("100") is not relative. Attribute 3 ("Family Size", section 93) is known ("1") and the attribute weight ("100") is not relative. Attribute 4 ("# Social Media", section 94) is known ("1") and the attribute weight ("50") is not Relative. Although not displayed, in some embodiments each attribute (section 95) could have components that are weighted and create an attribute score similar to the example of FIG. 5.

Furthermore, a list of prospective bill contributors (section 101) are listed in no particular order, and their attribute scores from the respective attributes culminate in a social profile number or score (section 100). Section 96 includes the prospective bill contributors' Zip Code attribute scores. Section 97 includes the prospective bill contributors' CPT attribute scores. Section 98 includes the prospective bill contributors' family size attribute scores, and section 99 indicates the prospective bill contributors' linked social media accounts attribute scores.

The sum of the distinct attribute scores uniquely produces a social profile number for the members 36 considered to be bill contributors. To even have a social profile number evaluated, the VSE platform 31 requires the members 36 to meet rigid criteria including participating in the same group association, and having the same state of residency as well as having known values for the particular social attributes being evaluated. However, it will be appreciated that these criteria may be different for different sharing networks 40.

The prospective members 36 being considered as bill contributors are then sorted by the greatest SPN to the least. In section 100, one (1) member ("Member 4") has the highest SPN ("314") and therefore the allocation module 42 will seek to draw from the available share balance within member's member share account (FIG. 1, SECTION 6) first. If there are not sufficient funds to offset the total of the given medical bill 38 or reserve request 41, then in addition to utilizing the funds from the member with the highest SPN, the allocation module 42 will repeat the evaluation until there are enough funds for the medical bill being allocated.

Referring additionally to the table 110 and section 111-116 of FIG. 7, in this example the medical bill "Amount Needed" is $828.16 (section 112). Section 111 shows the prospective bill contributors sorted in order of the greatest SPN, with the greatest being Member 4 ("314"). Member 4 has an available share balance (section 113) of $402.62. The allocation module 42 will debit (section 114) the total amount ($402.62), leaving Member 4 with $0.00 as their new available share balance (section 116), while $402.62 remains (section 115) to offset the entire amount needed. The process may repeat itself as needed, and it continues through the SPN sorted list for the first five (5) members. Member 2 begins the transaction with an available share balance (section 113) of $596.14, but the amount to debit (section 114) was only $102.46, leaving a new available share balance (section 116) of $493.68. However, with their contribution they would complete the search for the $828.16 (section 112), leaving the remaining prospective bill contributors untouched.

The VSE platform 31 may repeat this entire process immediately and automatically for each subsequent medical bill 38 or reserve request 41. However, any consequences to the available share balance for the prospective bill contributors from this transaction may be taken into account for each subsequent medical bill 38 or reserve request 41.

Features of the VSE platform 31 may include the social profile number (SPN) that is configured to represent a defined number of attributes of a share network member 36, and more particular an SPN that includes at least one group attribute or association or one geo location attribute. Furthermore, the VSE platform 31 enables a sharing network 40 to create multi-attributed SPNs and rank order (or weight) those attributes in terms of meaningful sharing. Furthermore, the VSE platform 31 provides for a social sharing service that combines first-in, first-out (FIFO) matching and allocation techniques, yet with the prioritization of matching members who share a weighting of social attributes.

Furthermore, the VSE platform 31 may enable sharing networks to create more meaningful sharing interactions by matching and allocating bill owners and contributors who share common attributes. The VSE computing platform 31 may also enable sharing networks 40 to prioritize sharing among members 36 linked to a defined group, and thus prioritizing and facilitating bill sharing between members 36 of multiple groups (within a single VSE/FBO Account). Moreover, the VSE platform 31 may also enable sharing networks 40 to prioritize sharing among members 36 linked to a defined geography (e.g., Town, City, MSA, State or Region), thus prioritizing and facilitating bill sharing between members of multiple geographies (within a single VSE/FBO Account). The VSE platform 31 may also advantageously enable a VSE platform operator to prioritize sharing among members 36 linked to a defined sharing network 40 within a single VSE/FBO account, allowing multiple sharing networks to exist within a single VSE/FBO Account.

As noted above, the VSE platform 31 may be implemented using one or more computing devices 31 such as servers, network interface devices, client devices, etc., including the appropriate hardware (e.g., processor, memory, etc.) and software having non-transitory computer readable instructions for performing the operations discussed herein. Moreover, in some embodiments the VSE platform 31 may be implemented within a cloud computing network. As noted above, it will be appreciated that the systems and methods set forth herein may also be used with other types of cost or expense sharing platforms besides healthcare sharing networks. That is, VSE platform may also support other share networks beyond just health care sharing, such as veterinary bills, automotive or appliance repairs, etc.

Figure 8:
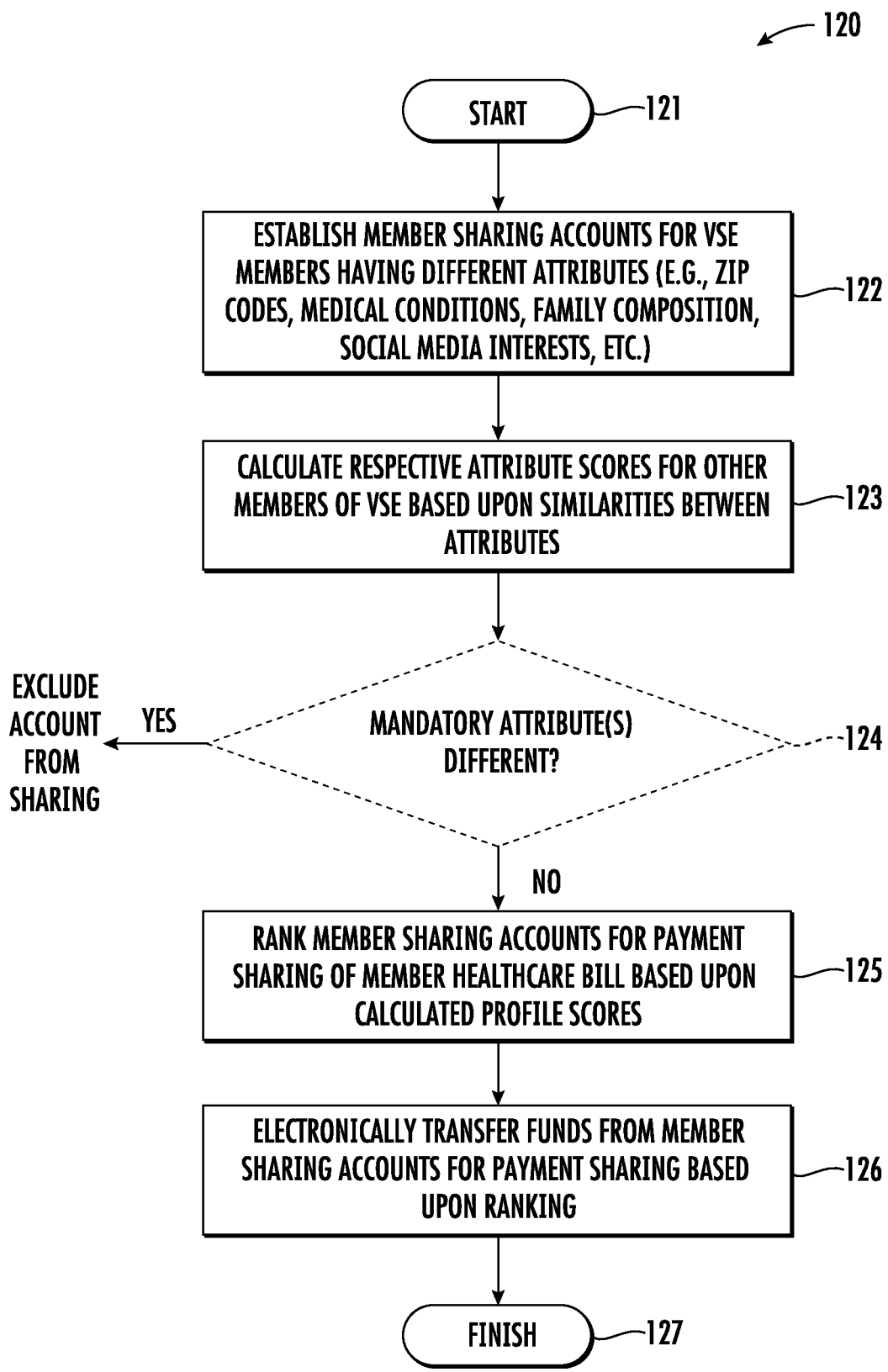
FIG. 8 is a flow diagram illustrating example method aspects associated with the computing device of FIG. 1.

Related method aspects are now described with reference to the flow diagram 120 of FIG. 8. Beginning at Block 121, the method illustrating includes, at a computing device (e.g., server) 34, establishing member sharing accounts 33 for respective members 36 of a VSE 40 for sharing payment of member healthcare bills 38 (or reserve requests 41) across the member sharing accounts, where the members have different associated attributes (Block 122). For a member healthcare bill 38 associated with a given member 36, the server 34 may further calculate respective attribute scores for the other members of the VSE 40 based upon similarities between the attributes of the other members and the attributes of the given member, at Block 123. In some embodiments, one or more of the attributes may optionally comprise mandatory attributes, and the server 34 may be configured to exclude from the ranking member sharing accounts of members 36 with the mandatory attribute different than (not matching) the mandatory attribute of the given member, at Block 124. If not excluded, the server 34 ranks the member sharing accounts 36 for payment sharing of the member healthcare bill 38 based upon the calculated attribute scores, at Block 125, and electronically transfers funds between the member sharing accounts 36 for payment sharing of the member healthcare bill based upon the ranking of the member sharing accounts (Block 126), as discussed further above. The method of FIG. 8 illustratively concludes at Block 127.

Many modifications and other embodiments will come to the mind of one skilled in the art having the benefit of the teachings presented in the foregoing descriptions and the associated drawings. Therefore, it is understood that the foregoing is not to be limited to the example embodiments, and that modifications and other embodiments are intended to be included within the scope of the appended claims.

That which is claimed is:

1. A computing device comprising:
a memory and a processor configured to cooperate with the memory to
establish member sharing accounts for respective members of a virtual share exchange (VSE) for sharing payment of member healthcare bills across the member sharing accounts, the members having different attributes associated therewith;
for a member healthcare bill associated with a given member, calculate respective attribute scores for the other members of the VSE based upon similarities between the attributes of the other members and the attributes of the given member by
dividing the attributes within a data structure into cascading components having successive parent/child data dependencies therebetween, and
calculating the respective attribute scores as a sum of successive score values for the other members with components matching those of the given member;
rank the member sharing accounts for payment sharing of the member healthcare bill based upon the calculated attribute scores; and
electronically transfer funds between the member sharing accounts for payment sharing of the member healthcare bill based upon the ranking of the member sharing accounts.

2. The computing device of claim 1 wherein at least one of the attributes comprises a mandatory attribute, and wherein the processor is configured to exclude from the ranking member sharing accounts of members with the mandatory attribute different than the mandatory attribute of the given member.

3. The computing device of claim 1 wherein the processor is further configured to aggregate the attribute scores into respective profile scores for each member, and rank the member sharing accounts for payment sharing based upon the profile scores.

4. The computing device of claim 1 wherein one of the attributes comprises zip codes associated with the members, and wherein the processor is configured to calculate zip code attribute scores for the other members based upon matching of at least a portion of their zip codes with a zip code of the given member.

5. The computing device of claim 4 wherein the processor is further configured to calculate respective state grouping, region, and area attribute scores for the other members from their zip codes based upon matches with a state grouping, region, and area associated with the zip code of the given member.

6. The computing device of claim 1 wherein one of the attributes comprises medical conditions, and wherein the processor is configured to calculate respective medical condition attribute scores based upon matching medical conditions of the other members with a medical condition of the given member.

7. The computing device of claim 6 wherein the processor is configured to determine the medical conditions of the members from Current Procedural Terminology (CPT) codes within at least one of a member medical history profile, and within the member medical bills submitted to the virtual share exchange.

8. The computing device of claim 1 wherein one of the attributes comprises family compositions of the members, and wherein the processor is configured to calculate family composition attribute scores based upon matching of family compositions of the other members with a family composition of the given member.

9. The computing device of claim 8 wherein the processor is further configured to calculate respective number of participants, gender, and age attribute scores for the other members based upon matches with a number of participants, genders, and ages associated with the family of the given member.

10. The computing device of claim 1 wherein one of the attributes comprises social media interests, and wherein the processor is configured to calculate social media interest attribute scores based upon matching of social media interests of the other members with social media interests of the given member for member social media accounts linked to the member sharing accounts.

11. A method comprising:
establishing, at a server, member sharing accounts for respective members of a virtual share exchange (VSE) for sharing payment of member healthcare bills across the member sharing accounts, the members having different attributes associated therewith;
for a member healthcare bill associated with a given member, calculating respective attribute scores at the server for the other members of the VSE based upon similarities between the attributes of the other members and the attributes of the given member by
dividing the attributes within a data structure into cascading components having successive parent/child data dependencies therebetween, and
calculating the respective attribute scores as a sum of successive score values for the other members with components matching those of the given member;
ranking, at the server, the member sharing accounts for payment sharing of the member healthcare bill based upon the calculated attribute scores; and
electronically transferring funds at the server between the member sharing accounts for payment sharing of the member healthcare bill based upon the ranking of the member sharing accounts.

12. The method of claim 11 wherein one of the attributes comprises zip codes associated with the members, and wherein calculating comprises calculating zip code attribute scores for the other members based upon matching of at least a portion of their zip codes with a zip code of the given member.

13. The method of claim 11 wherein one of the attributes comprises medical conditions, and wherein calculating comprises calculating respective medical condition attribute scores based upon matching medical conditions of the other members with a medical condition of the given member.

14. The method of claim 11 wherein one of the attributes comprises family compositions of the members, and wherein calculating comprises calculating family composition attribute scores based upon matching of family compositions of the other members with a family composition of the given member.

15. The method of claim 11 wherein one of the attributes comprises social media interests, and wherein calculating comprises calculating social media interest attribute scores based upon matching of social media interests of the other members with social media interests of the given member for member social media accounts linked to the member sharing accounts.

16. A non-transitory computer-readable medium having computer-executable instructions for causing a computing device to perform steps comprising:
establishing member sharing accounts for respective members of a virtual share exchange (VSE) for sharing payment of member healthcare bills across the member sharing accounts, the members having different attributes associated therewith;
for a member healthcare bill associated with a given member, calculating respective attribute scores for the other members of the VSE based upon similarities between the attributes of the other members and the attributes of the given member by
dividing the attributes within a data structure into cascading components having successive parent/child data dependencies therebetween, and
calculating the respective attribute scores as a sum of successive score values for the other members with components matching those of the given member;
ranking the member sharing accounts for payment sharing of the member healthcare bill based upon the calculated attribute scores; and
electronically transferring funds between the member sharing accounts for payment sharing of the member healthcare bill based upon the ranking of the member sharing accounts.

17. The non-transitory computer-readable medium of claim 16 wherein one of the attributes comprises zip codes associated with the members, and wherein calculating comprises calculating zip code attribute scores for the other members based upon matching of at least a portion of their zip codes with a zip code of the given member.

18. The non-transitory computer-readable medium of claim 16 wherein one of the attributes comprises medical conditions, and wherein calculating comprises calculating respective medical condition attribute scores based upon matching medical conditions of the other members with a medical condition of the given member.

19. The non-transitory computer-readable medium of claim 16 wherein one of the attributes comprises family compositions of the members, and wherein calculating comprises calculating family composition attribute scores based upon matching of family compositions of the other members with a family composition of the given member.

20. The non-transitory computer-readable medium of claim 16 wherein one of the attributes comprises social media interests, and wherein calculating comprises calculating social media interest attribute scores based upon matching of social media interests of the other members with social media interests of the given member for member social media accounts linked to the member sharing accounts.

* * * * *